United States Patent
Keim et al.

(10) Patent No.: US 6,310,259 B1
(45) Date of Patent: Oct. 30, 2001

(54) METHOD FOR PRODUCING 6,10 AND 6,9-DIMETHYL-5,10-UNDECADIENYL-2-ONES

(75) Inventors: Wilhelm Keim; Armin Kraus, both of Aachen; Rainer Hahn, Karlstein; Klaus Huthmacher, Geinhausen, all of (DE)

(73) Assignee: Degussa AG (DE)

( * ) Notice: Subject to any disclaimer, the term of this patent is extended or adjusted under 35 U.S.C. 154(b) by 0 days.

(21) Appl. No.: 09/446,734
(22) PCT Filed: Jun. 17, 1998
(86) PCT No.: PCT/EP98/03647
 § 371 Date: Mar. 23, 2000
 § 102(e) Date: Mar. 23, 2000
(87) PCT Pub. No.: WO99/03811
 PCT Pub. Date: Jan. 28, 1999

(30) Foreign Application Priority Data

Jul. 17, 1997 (DE) ............................................. 197 30 546

(51) Int. Cl.[7] .................................................. C07C 45/00
(52) U.S. Cl. ........................ 568/398; 568/397; 568/417
(58) Field of Search ................................. 568/354, 356, 568/397, 398, 417

(56) References Cited

U.S. PATENT DOCUMENTS 3,914,289 * 10/1975 Akutagawa et al. .

* cited by examiner

Primary Examiner—Jean F. Vollano
(74) Attorney, Agent, or Firm—Smith, Gambrell & Russell, LLP

(57) ABSTRACT

The present application refers to a process for preparing 6,10- and 6,9-dimethyl-5,10-undecadienyl-2-ones by telomerizing isoprene with alkyl acetoacetates in the presence of a catalyst system containing a transition metal compound catalyst and a phosphorus- or arsenic-containing compound cocatalyst, wherein the process is performed in the presence of a protic additive of the general formula $$R^1\text{---OH,} \quad (I)$$

or $$\left[\begin{array}{c} R^1 \\ \backslash \\ R^2\text{---NH}^+ \\ / \\ R^3 \end{array}\right]_y X^{(-)y} \quad (II)$$

in which:

$R^1$, $R^2$, $R^3$ represent an alkyl group with 1 to 9 carbon atoms, branched or unbranched, a cycloalkyl group with 6 to 8 carbon atoms, an aryl group, in particular phenyl, or an arylalkyl group, $X^{(-)}$ represents an inorganic or organic anion, y is 1 or 2, and the β-ketoester so obtained is saponified and decarboxylated in a manner known per se.

20 Claims, No Drawings

METHOD FOR PRODUCING 6,10 AND 6,9-DIMETHYL-5,10-UNDECADIENYL-2-ONES

BACKGROUND OF THE INVENTION

The invention relates to a process for preparing 6,10- and 6,9-dimethyl-5,10-undecadienyl-2-ones by telomerizing isoprene with alkylacetoacetates using transition metal compounds as catalysts, followed by saponification and decarboxylation of the β-ketoester obtained.

When using the asymmetric diene, isoprene, there are 12 possible telomeric products, taking into account the linkage pattern of isoprene units in the direction of attack of the nucleophile in the 1, or 3 position and the E,Z-isomerism of the internal double bond. This number is potentiated by using a nucleophile with several acid hydrogen atoms.

Of the 12 possible telomeric products, three have the desired head-to-tail linkage pattern analogous to that in naturally occurring products.

Hitherto, processes disclosed in the prior art have only led to products in which a very small percentage of this type of telomer, if any, can be detected. A process for the preparation of octadienyl hydrocarbon chains is known from J. Berger, *J. für prakt. Chem.* 327 (1985) 634. Selectivities relating to head-to-tail linkages of <8% are obtained using the route described there.

In G. Hata, J. Org. Chem. 1971 (15), 2116 and Zakharkin et 30 al., *Zh. Org. Khim.* 1988, (24) 2325, no reference is made to the production of compounds with the desired heads-to-tail linkage when using the reaction mentioned.

Compounds of this type, in particular α-geranylacetone, however, are of great importance as key components for the synthesis of vitamin E.

OBJECT OF THE INVENTION

The object of the invention is to provide a process in which this compound and also related compounds are obtained, these having been proven to be valuable intermediates.

SUMMARY OF THE INVENTION

The invention provides a process for preparing 6,10- and 6,9-dimethyl-5,10-undecadienyl-2-ones by telomerizing isoprene with alkyl acetoacetates in the presence of a catalyst system consisting of transition metal compound catalyst and a phosphorus- or arsenic-containing compound cocatalyst, characterized in that the process is performed in the presence of a protic additive of the general formula:

$$R^1\text{---}OH, \quad (I)$$

or

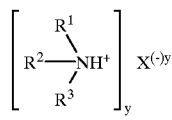

in which:

R$^1$, R$^2$, R$^3$ represent an alkyl group with 1 to 9 carbon atoms, branched or unbranched, a cycloalkyl group with 6 to 8 carbon atoms, an aryl group, a phenyl, or an arylalkyl group, X$^{(-)}$ represents an inorganic or organic anion, in particular halide or sulfate, y is 1 or 2 and the β-ketoester so obtained is saponified and decarboxylated in a manner known per se. The invention provides 6,10-isomers in particular.

DETAILED DESCRIPTION

In the process of the present invention aliphatic carboxylic acids with 1 to 6 carbons, arylsulfonic acids or alkylsulfonic acids can be used in addition to or instead of the protic additives in accordance with formulae (I) or (II).

Organic solvents are optionally used and are not restricted to specific compounds, with the exception of the general principle that they behave in an inert manner, in the sense of a chemical reaction.

Thus, a protonizing effect is not intended, as is the case, for example, with alcohols of the general formula (I) in the present reaction.

The solvents are also used in the form of mixtures, wherein compounds in accordance with formula (I) act simultaneously as protic additives and as solvents. For example, the present process can be performed in the presence of an organic solvent. Aromatic solvents such as benzene, toluene or phenol, and also alkyl-substituted phenols, ketones and aliphatic alcohols, are suitable solvents.

In a specific embodiment, the compound of the Formula (I), optionally mixed with non-protic solvents, is used a solvent.

Alkyl acetoacetates useful in the present invention are those represented by the general formula

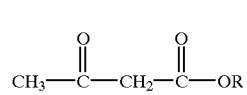

in which

R represents a $C_1$–$C_4$ alkyl group, branched or unbranched.

In the present invention, it is preferred that at least two equivalents of isoprene are reacted with one equivalent of an alkyl acetoacetate of formula (III).

The present catalyst system consists of a transition metal from groups 9 and 10 of the Periodic System of Elements (IUPAC 1985) or compounds thereof, and a cocatalyst consisting of a compound of the general formula $$A\,(R^4\ R^5\ R^6) \quad (IV)$$

in which

R$^4$, R$^5$, R$^6$ are identical or different and represent an alkyl or alkoxy group with 1 to 8 carbon atoms, branched or unbranched, a cycloalkyl group with 6 to 8 carbon atoms, an aryl group, in particular phenyl, optionally substituted, preferably substituted in the 2-position and/or 5-position with an alkyl group, an arylalkyl group, or hydrogen;

A represents phosphorus or arsenic.

Preferably, at least one of the substituents R$^4$, R$^5$, R$^6$ is itself substituted by one of the groups comprising OH, —NR$^1$H, NR$^1$R$^2$H(+) or —COOH, wherein R$^1$ and R$^2$ are defined in the same way as above.

Phosphorus- or arsenic-containing compounds in accordance with formula (IV) are preferably used as cocatalysts, in which at least one of the substituents represents an alkoxy group, in particular a $C_3$ group. 1 to 10 equivalents of phosphorus- or arsenic-containing compounds according to Formula IV are used to one equivalent of the transition metal or its ions.

The transition metal catalyst useful in the present process is used in an amount sufficient to provide up to $10^{-4}$ to 1 g atom/l of elemental metal. Examples of transition metal compounds or transition metal ligands useful as catalysts in the present process are acetate, carboxylate, carbonate, borate, citrate, bromide, chloride, iodide, hydroxide, nitrate, sulfate, arylsulfonate, alkylsulfonate, acetylacetonate, palladium bis-benzonitrile or potassium tetrapalladate. A palladium-containing compound is particularly preferred in the present invention.

The reaction of the present invention is optionally performed in the presence of a compound, which acts as a reducing agent for the transition metal. Examples of such reducing agent are sodium borohydride, potassium borohydride, zinc powder or magnesium. In combination with isopropanol as solvent, particularly high selectivities are obtained.

In a specific embodiment of the present invention, the 6,10-dimethyl-5,10-undecadienyl-2-one and 6,9-dimethyl-5,10-undecadienyl-2-one are separated from the reaction mixture.

In these cases, Pd acetate is used as the catalyst. The 3-head-to-tail isomers produced in addition to the selectively prepared α-geranylacetone (1-head-to-tail) is another valuable product of this reaction.

Optionally, it has proven advantageous to perform the process in several phases in order, for example, to be able to separate the catalyst or the product(s) more easily.

The selectivities can be controlled by suitable combinations of temperature, solvent and cocatalyst.

The process of the present invention is performed at a temperature of from 0° C. to 130° C., in particular of from 60° C. to 100° C.

EXAMPLE 1

Using a protective gas technique (Ar)-, 11.2 mg (0.05 mmol) of palladium acetate and 39.3 mg (0.15 mmol) of triphenyl phosphane were transferred at 0° C. with 20 ml of i-propanol into a 50 ml glass autoclave with a magnetic stirring rotor. The homogeneous, yellow solution obtained after the addition of 6 g of ethyl acetoacetate and 6.5 g of isoprene was stirred for 3 h at 80° C. and then cooled to room temperature in an ice bath. Then the excess isoprene was removed at room temperature under a water-jet vacuum.

The ethyl-2-(dimethyloctadienyl)-β-ketoesters contained in the reaction mixture were saponified and decarboxylated without further processing. For this purpose, the reaction mixture was stirred for 16 h at room temperature, after adding 3.8 g of sodium hydroxide, 15 ml of water and 30 ml of methanol. After the majority of the solvent had been removed on a rotary evaporator at 80° C., 30 ml of water and 6.4 g of concentrated sulfuric acid were added to the mixture and heated under reflux until no more carbon dioxide was produced (about 1 hour). After extracting three times, using 5 ml of toluene each time, the combined extracts were dried over sodium sulfate. Gas chromatographic analysis of the crude product showed a yield of isogeranylacetones of 29% (with respect to the isoprene used) with a selectivity for 6,10-dimethyl-5,10-undecadien-2-one of 30% (with respect to the telomer fraction).

EXAMPLES 2–40

The same procedure was used as described in Example 1. The addition of 20 ml of i-propanol used there was replaced by 20 ml of another compound, in accordance with Table 1, each time. Against this is plotted the turn-over number $mol_{product}$ $mol_{pd}^{-1}$), TON, and the selectivity for 6,10-dimethyl-5,10-undecadien-2-one, 1-HT, with respect to the telomer fraction.

Table 1: Turn-over numbers $mol_{product}$ $mol_{pd}^{-1}$) and head-to-tail selectivities (with respect to the telomer fraction) as a function of the additive used and the reaction temperature ($n_{Pd}$:$n_P$:$n_{acetate}$:$n_{isoprene}$=1:3:920:1920, t=3 h).

EXAMPLES 41–69

The same procedure was used as described in Example 1. The addition of 20 ml of i-propanol used there was replaced by 20 ml of a compound, in accordance with the table. Triphenyl phosphane was replaced by another phosphorus compound in accordance with the table. Against this is plotted the turn-over number {$mol_{product}$ $mol_{Pd}^{-1}$), TON, and the selectivity for 6,10-dimethyl-5,10-undecadien-2-one, 1-HT, with respect to the telomer fraction.

Table 2: Turn-over numbers {$mol_{product}$ $mol_{pd}^{-1}$) and head-tail selectivities (with respect to the telomer fraction} as a function of the phosphorus compound and additive used ($n_{Pd}$: $n_P$: $n_{acetate}$: $n_{isoprene}$=1:3:920:1920, t=3 h).

TABLE 1

| | | | | Proportion of telomer fraction/% | | | | | | | |
|---|---|---|---|---|---|---|---|---|---|---|---|
| Example | Cocatalyst | T ° C. | Reaction medium | 1HT | 1TT | 1TH | 1HH | 3HT | 3TT | Other | ton |
| 2 | PPh3 | 80 | Acetone | 4.2 | 86.6 | 4.6 | 0.4 | 0.7 | 3.0 | 0.6 | 298 |
| 3 | PPh3 | 80 | Toluene | 3.3 | 83.6 | 3.3 | 0.3 | 0.0 | 2.8 | 6.5 | 29 |
| 4 | PPh3 | 80 | Isoprene | 3.3 | 83.9 | 3.0 | 0.7 | 0.4 | 2.7 | 6.0 | 31 |
| 5 | PPh3 | 80 | t-pentanol | 24.0 | 59.1 | 10.1 | 1.1 | 3.4 | 2.0 | 0.3 | 276 |
| 6 | PPh3 | 80 | Methylene chloride | 15.5 | 65.6 | 11.7 | 1.1 | 2.8 | 2.5 | 0.8 | 102 |
| 7 | PPh3 | 80 | t-butanol | 27.1 | 53.7 | 11.9 | 1.3 | 3.5 | 1.9 | 0.5 | 371 |
| 8 | PPh3 | 80 | Acetonitrile | 18.4 | 61.2 | 13.0 | 1.2 | 2.7 | 2.6 | 0.9 | 173 |
| 9 | PPh3 | 80 | n-pentanol | 28.0 | 36.8 | 26.9 | 3.8 | 2.7 | 1.2 | 0.7 | 401 |
| 10 | PPh3 | 80 | I—PrOH/H2O | 18.6 | 43.6 | 31.2 | 4.0 | 1.4 | 0.7 | 0.5 | 59 |
| 11 | PPh3 | 80 | Pinacol | 27.2 | 32.6 | 30.6 | 5.0 | 2.2 | 1.4 | 0.9 | 123 |
| 12 | PPh3 | 80 | Ethanol | 28.3 | 30.7 | 32.1 | 5.7 | 1.8 | 1.1 | 0.4 | 207 |
| 13 | PPh3 | 80 | Methanol | 16.0 | 25.3 | 47.0 | 8.3 | 0.8 | 0.8 | 1.7 | 42 |
| 14 | PPh3 | 80 | Phenol | 1.0 | 1.0 | 80.7 | 17.4 | 0.0 | 0.0 | 0.0 | 6 |
| 15 | PPh3 | 80 | 2,6-dimethylphenol | 1.6 | 6.9 | 53.0 | 27.3 | 0.0 | 1.9 | 9.3 | 197 |
| 16 | PPh3 | 80 | 2,3-butanediol | 10.9 | 0.9 | 39.5 | 40.0 | 0.0 | 0.0 | 8.7 | n.d. |
| 17 | PPh3 | 80 | t-butylphenol | 2.7 | 4.3 | 36.9 | 54.4 | 0.0 | 0.0 | 1.7 | 150 |
| 18 | PPh3 | 80 | i-propylphenol | 1.6 | 1.7 | 25.4 | 58.1 | 0.0 | 0.0 | 13.2 | 157 |

TABLE 1-continued

| | | | | Proportion of telomer fraction/% | | | | | | | |
|---|---|---|---|---|---|---|---|---|---|---|---|
| Example | Cocatalyst | T ° C. | Reaction medium | 1HT | 1TT | 1TH | 1HH | 3HT | 3TT | Other | ton |
| 19 | PPh3 | 80 | 2,4,6-trichlorophenol | n.d. | n.d. | n.d. | n.d. | n.d. | n.d. | 100a | <2 |
| 20 | PPh3 | 80 | Propionic acid | n.d. | n.d. | n.d. | n.d. | n.d. | n.d. | 100a | <2 |
| 21 | PPh3 | 50 | i-propanol | n.d. | n.d. | n.d. | n.d. | n.d. | n.d. | n.d. | <1 |
| 22 | PPh3 | 60 | i-propanol | 5.8 | 11.8 | 66.3 | 10.4 | 0.0 | 0.0 | 5.8 | 2 |
| 23 | PPh3 | 70 | i-propanol | 22.3 | 19.5 | 39.7 | 6.5 | 1.8 | 1.2 | 9.0 | 16 |
| 24 | PPh3 | 75 | i-propanol | 26.0 | 22.9 | 36.0 | 5.8 | 1.6 | 0.8 | 7.0 | 30 |
| 25 | PPh3 | 85 | i-propanol | 28.4 | 39.6 | 23.5 | 3.1 | 2.8 | 1.5 | 1.2 | 396 |
| 26 | PPh3 | 90 | i-propanol | 30.5 | 39.5 | 21.8 | 2.9 | 2.8 | 1.6 | 0.9 | 247 |
| 27 | PPh3 | 70 | t-pentanol | 29.4 | 38.5 | 19.1 | 2.5 | 2.4 | 1.3 | 6.7a | |
| 28 | PPh3 | 50 | t-butanol | 27.9 | 24.9 | 34.5 | 5.7 | 2.2 | 1.0 | 3.9 | 27 |
| 29 | PPh3 | 60 | t-butanol | 32.6 | 35.8 | 23.5 | 3.1 | 3.5 | 1.2 | 0.4 | 159 |
| 30 | PPh3 | 70 | t-butanol | 31.0 | 44.1 | 17.1 | 1.9 | 3.9 | 1.5 | 0.6 | 2B6 |
| 31 | PPh3 | 90 | t-butanol | 18.2 | 65.9 | 9.3 | 1.0 | 2.3 | 2.3 | 1.0 | 458 |
| 32 | PPh3 | 60 | n-pentanol | 24.3 | 26.6 | 37.7 | 8.7 | 1.6 | 1.2 | 0.0 | 52 |
| 33 | PPh3 | 70 | n-pentanol | 28.0 | 27.7 | 34.9 | 6.3 | 2.0 | 1.2 | 0.0 | 134 |
| 34 | PPh3 | 85 | n-pentanol | 28.0 | 36.8 | 26.9 | 3.8 | 2.7 | 1.2 | 0.7 | 401 |
| 35 | PPh3 | 90 | n-pentanol | 28.8 | 41.9 | 22.9 | 2.9 | 0.6 | 1.6 | 0.7 | 425 |
| 36 | PPh3 | 60 | Ethanol | 27.1 | 27.6 | 35.2 | 7.3 | 1.3 | 0.9 | 0.9 | 23 |
| 37 | PPh3 | 70 | Ethanol | 26.2 | 27.6 | 35.9 | 7.1 | 1.5 | 1.0 | 0.5 | 87 |
| 38 | PPh3 | 90 | Ethanol | 27.0 | 36.1 | 28.4 | 4.0 | 2.2 | 1.4 | 1.0 | 425 |
| 39 | PPh3 | 60 | i-propylphenol | 0.0 | 0.0 | 0.0 | 13.5 | 0.0 | 0.0 | 86.5 | 3 |
| 40 | PPh3 | 70 | i-propylphenol | 0.8 | 2.3 | 15.5 | 51.8 | 0.0 | 0.0 | 29.5 | 21 |

TABLE 2

| | | | | Proportion of telomer fraction/% | | | | | | | |
|---|---|---|---|---|---|---|---|---|---|---|---|
| Example | Cocatalyst | T ° C. | Reaction medium | 1HT | 1TT | 1TH | 1HH | 3HT | 3TT | Other | ton |
| 41 | P(CH2CH2CH2CH3)3 | 80 | Aceton | 15.7 | 38.0 | 36.2 | 5.3 | 1.5 | 1.8 | 1.6 | 70 |
| 42 | PPh(CH2CH2CH3)2 | 80 | Acetone | 18.1 | 50.6 | 23.9 | 1.8 | 2.0 | 1.9 | 1.7 | 138 |
| 43 | PPh2(CH2CH2CH3) | 80 | Acetone | 17.3 | 51.7 | 23.1 | 2.1 | 1.7 | 1.7 | 2.5 | 99 |
| 44 | PPh(OCH2CH2CH2CH3)2 | 80 | Acetone | 12.5 | 66.4 | 7.7 | 0.9 | 0.9 | 1.2 | 10.5 | 298 |
| 45 | PPh2(OCH2CH2CHCH3) | 80 | Acetone | 4.0 | 83.7 | 6.5 | 0.5 | 0.4 | 2.0 | 2.8 | 69 |
| 46 | P(OCH2CH2CH2CH3)3 | 80 | Acetone | 19.0 | 72.6 | 3.5 | 0.4 | 1.3 | 3.0 | 0.2 | 408 |
| 47 | 2-PPh$_2$cyclopentanol | 80 | Acetone | 4.9 | 75.3 | 13.8 | 1.2 | 1.1 | 1.8 | 2.0 | 42 |
| 48 | P(Ph)$_2$(CH$_2$CH$_2$CH$_2$OH) | 80 | Acetone | 20.3 | 56.5 | 16.5 | 1.6 | 2.0 | 1.9 | 1.0 | 75 |
| 49 | P(CH2CH2CH2CH3)3 | 80 | i-propanol | 8.9 | 9.1 | 51.8 | 19.8 | 0.8 | 0.7 | 8.7 | 555 |
| 50 | P(o-anisyl)3 | 80 | i-propanol | 15.7 | 21.2 | 36.4 | 26.4 | 0.2 | 0.0 | 0.1 | 24 |
| 51 | P(p-Me2NC6H4)3 | 80 | i-propanol | 10.9 | 23.0 | 44.4 | 20.8 | 0.3 | 0.0 | 0.6 | 12 |
| 52 | PPh(CH2CH2CH3)2 | 80 | i-propanol | 12.5 | 15.1 | 59.9 | 12.5 | 0.0 | 0.0 | 0.0 | 3 |
| 53 | PPh2(CH2CH2CH3) | 80 | i-propanol | 28.5 | 26.6 | 31.9 | 7.0 | 1.7 | 0.8 | 3.4 | 264 |
| 54 | P(p-tol)3 | 80 | i-propanol | 28.6 | 28.6 | 33.5 | 6.0 | 1.6 | 1.2 | 0.6 | 72 |
| 55 | PPh(OCH2CH2CH2CH3)2 | 80 | i-propanol | 41.9 | 33.3 | 18.7 | 2.8 | 2.2 | 0.8 | 0.2 | 216 |
| 56 | PPh2(OCH2CH2CHCH3) | 80 | i-propanol | 27.6 | 49.4 | 16.3 | 1.7 | 2.6 | 0.7 | 1.7 | 396 |
| 57 | P(OCH2CH2CH2CH3)3 | 80 | i-propanol | 39.5 | 40.0 | 14.4 | 1.6 | 2.9 | 1.6 | 0.0 | 540 |
| 58 | P(OEt)3 | 80 | i-propanol | 35.1 | 47.0 | 12.1 | 1.4 | 2.9 | 1.1 | 0.5 | 262 |
| 59 | P(O-i-octyl)3 | 80 | i-propanol | 36.3 | 47.7 | 10.0 | 1.1 | 2.8 | 1.6 | 0.4 | 468 |
| 60 | P(OCH2)3CCH3a) | 80 | i-propanol | 36.8 | 50.6 | 7.4 | 0.8 | 2.8 | 1.3 | 0.2 | 129 |
| 61 | P(OCH2)3CCH2OHb) | 80 | i-propanol | 34.9 | 52.8 | 7.0 | 0.8 | 2.8 | 1.1 | 0.5 | 229 |
| 62 | P(OCH2)3CCH2OH | 80 | i-propanol | 34.9 | 52.8 | 7.0 | 0.8 | 2.8 | 1.1 | 0.5 | 459 |
| 63 | P(OPH)$_3$ | 80 | i-propanol | 18.6 | 72.9 | 5.2 | 0.5 | 1.2 | 0.5 | 1.1 | 272 |
| 64 | P(CH$_2$CH$_2$CN)$_3$ | 80 | i-propanol | n.d. | n.d. | n.d. | n.d. | n.d. | n.d. | n.d. | <2 |
| 65 | P(Ome)$_3$ | 80 | i-propanol | n.d. | n.d. | n.d. | n.d. | n.d. | n.d. | n.d. | <2 |
| 66 | P(O-2,6-dimethylphenyl)$_3$ | 80 | i-propanol | n.d. | n.d. | n.d. | n.d. | n.d. | n.d. | n.d. | <2 |
| 67 | P(pentafluorophenyl)$_3$ | 80 | i-propanol | n.d. | n.d. | n.d. | n.d. | n.d. | n.d. | n.d. | <2 |
| 68 | P(OCH$_2$CF$_3$)$_3$ | 80 | i-propanol | n.d. | n.d. | n.d. | n.d. | n.d. | n.d. | n.d. | <2 |
| 69 | Pd(P(OCH$_2$)$_3$CCH$_2$OH)$_4$ | 80 | i-propanol | 24.6 | 64.9 | 2.6 | 4.0 | 1.8 | 1.7 | 0.3 | 111 |
| 70 | ppH$_2$(O—H—C$_6$H$_4$) | 80 | i-propanol | n.d. | n.d. | n.d. | n.d. | n.d. | n.d. | n.d. | <2 |

TABLE 3

Formulation same as in examples 41–70, with variable temperature

| | | | | Proportion of telomer fraction/% | | | | | | | |
|---|---|---|---|---|---|---|---|---|---|---|---|
| Example | Cocatalyst | T ° C. | Reaction medium | 1HT | 1TT | 1TH | 1HH | 3HT | 3TT | Other | ton |
| 71 | P(Obu)3 | 50 | EtOH | 17.2 | 16.8 | 39.9 | 26.1 | 0.0 | 0.0 | 0.0 | 2 |
| 72 | P(Obu)3 | 60 | EtOH | 22.5 | 24.3 | 36.7 | 16.5 | 0.0 | 0.0 | 0.0 | 2 |
| 73 | P(Obu)3 | 70 | EtOH | 9.1 | 6.4 | 53.8 | 10.2 | 0.5 | 0.8 | 19.1 | 29 |
| 74 | P(Obu)3 | 90 | EtOH | 23.0 | 32.3 | 36.8 | 4.1 | 1.7 | 0.7 | 1.4 | 446 |
| 75 | P(Obu)3 | 80 | t-butanol | 15.0 | 75.1 | 5.6 | 0.6 | 1.1 | 9.0 | 1.6 | 456 |
| 76 | P(Obu)3 | 90 | t-butanol | 32.7 | 55.9 | 5.9 | 0.7 | 2.1 | 2.3 | 0.4 | 512 |
| 77 | P(Obu)3 | 90 | 2-propanol | 34.4 | 49.8 | 10.1 | 1.0 | 2.5 | 1.4 | 0.6 | 377 |
| 78 | P(Obu)3 | 70 | t-butanol | 40.9 | 43.5 | 9.5 | 1.2 | 2.7 | 1.8 | 0.3 | 305 |
| 79 | P(Obu)3 | 70 | 2-propanol | 40.5 | 35.5 | 16.0 | 2.0 | 3.3 | 1.5 | 1.3 | 326 |
| 80 | P(Obu)3 | 60 | 2-propanol | 38.0 | 32.9 | 18.2 | 2.2 | 2.7 | 1.3 | 4.8 | 357 |
| 81 | P(Obu)3 | 50 | t-butanol | 41.2 | 33.2 | 18.5 | 2.7 | 2.8 | 1.3 | 0.3 | 92 |
| 82 | P(Obu)3 | 50 | 2-propanol | 31.9 | 24.6 | 32.6 | 7.1 | 2.0 | 1.0 | 0.7 | 68 |
| 83 | P(Obu)3 | 60 | t-butanol | 21.4 | 19.4 | 23.4 | 29.6 | 0.0 | 0.0 | 6.2 | 3 |
| 84 | P(OCH2)3CCH2OH | 50 | Ethanol | 4.5 | 4.5 | 44.3 | 46.6 | 0.0 | 0.0 | 0.0 | 1 |
| 85 | P(OCH2)3CCH2OH | 60 | Ethanol | 36.1 | 38.5 | 22.7 | 2.7 | 0.0 | 0.0 | 0.0 | 24 |
| 86 | P(OCH2)3CCH2OH | 70 | Ethanol | 23.6 | 24.7 | 26.0 | 13.5 | 1.4 | 1.2 | 9.6 | 26 |
| 87 | P(OCH2)3CCH2OH | 80 | Ethanol | 26.1 | 26.1 | 21.4 | 10.2 | 1.5 | 1.3 | 13.5 | 34 |
| 88 | P(OCH2)3CCH2OH | 90 | Ethanol | 36.7 | 43.2 | 1.8 | 3.3 | 2.4 | 1.0 | 0.6 | 123 |
| 89 | P(OCH2)3CCH2OH | 50 | 2-propanol | 30.0 | 27.7 | 23.4 | 6.8 | 2.2 | 1.0 | 8.7 | 25 |
| 90 | P(OCH2)3CCH2OH | 60 | 2-propanol | 38.4 | 37.5 | 12.7 | 1.7 | 3.0 | 1.2 | 5.5 | 69 |
| 91 | P(OCH2)3CCH2OH | 70 | 2-propanol | 39.0 | 43.9 | 8.6 | 1.1 | 2.7 | 1.3 | 3.4 | 106 |
| 92 | P(OCH2)3CCH2OH | 90 | 2-propanol | 33.6 | 56.8 | 5.0 | 0.7 | 2.0 | 1.5 | 0.3 | 511 |
| 93 | P(OCH2)3CCH2OH | 80 | Methanol | 5.0 | 12.9 | 48.8 | 27.6 | 0.0 | 0.0 | 5.6 | 8 |
| 94 | P(OCH2)3CCH2OH | 50 | t-butanol | 35.4 | 37.3 | 11.8 | 8.1 | 2.3 | 1.1 | 4.0 | 20 |
| 95 | P(OCH2)3CCH2OH | 60 | t-butanol | 36.4 | 45.7 | 7.4 | 4.4 | 2.6 | 1.3 | 2.2 | 631 |
| 96 | P(OCH2)3CCH2OH | 70 | t-butanol | 34.8 | 52.4 | 5.0 | 1.4 | 2.5 | 1.5 | 2.5 | 105 |
| 97 | P(OCH2)3CCH2OH | 80 | t-butanol | 30.0 | 61.1 | 3.3 | 0.9 | 2.1 | 1.9 | 0.7 | 123 |
| 98 | P(OCH2)3CCH2OH | 90 | t-butanol | 23.8 | 68.4 | 3.2 | 0.6 | 1.8 | 2.0 | 0.3 | 404 |

TABLE 4

Formulation same as in examples 1, with variable telogens and solvents

| | | | Proportion of telomer fraction/% | | | | | | | |
|---|---|---|---|---|---|---|---|---|---|---|
| Example | Reaction medium | Telogen | 1HT | 1TT | 1TH | 1HH | 3HT | 3TT | Other | ton |
| 99 | Acetone | CH$_3$COCH$_2$COOCH$_3$ | 10.6 | 45.4 | 24.9 | 1.9 | 2.0 | 2.4 | 12.6 | 14 |
| 100 | Acetone | CH$_3$COCH$_2$COOC(CH$_3$)$_3$ | 5.3 | 34.3 | 12.6 | 2.1 | 2.9 | 0.0 | 42.7 | 30 |
| 101 | Acetone | (CH$_3$CO)$_2$CHCOOCH$_3$ | 9.7 | 21.7 | 54.8 | 5.6 | 0.0 | 1.1 | 7.1 | 31 |
| 102 | i-PrOH | CH$_3$COCH$_2$COOCH$_3$ | 24.9 | 28.4 | 35.8 | 6.2 | 2.3 | 1.1 | 1.4 | 150 |
| 103 | i-PrOH | CH$_3$COCH$_2$COOC(CH$_3$)$_3$ | 20.3 | 38.1 | 33.2 | 3.9 | 0.2 | 0.7 | 3.5 | 86 |
| 104 | i-PrOH | (CH$_3$CO)$_2$CHCOOCH$_3$ | 7.8 | 16.1 | 56.5 | 14.9 | 0.0 | 0.0 | 4.7 | 18 |

TABLE 5

Formulation same as in examples 1, with variable solvent telogen concentration

| | | | Proportion of telomer fraction/% | | | | | | | |
|---|---|---|---|---|---|---|---|---|---|---|
| Example | Reaction medium | acetate:Pd | 1HT | 1TT | 1TH | 1HH | 3HT | 3TT | Other | ton |
| 105 | i-PrOH | 200:1 | 21.9 | 28.3 | 36.8 | 5.4 | 1.4 | 1.2 | 2.0 | 14 |
| 106 | i-PrOH | 400:1 | 28.9 | 27.7 | 30.5 | 5.4 | 0.4 | 1.0 | 3.0 | 65 |
| 107 | i-PrOH | 1800:1 | 28.5 | 24.6 | 27.2 | 4.6 | 0.2 | 0.5 | 10.8 | 88 |
| 108 | i-PrOH | 2500:1 | 26.4 | 23.7 | 25. | 4.4 | 2.3 | 0.6 | 13.9 | 46 |
| 109 | i-PrOH | 3400:1 | 21.1 | 14.9 | 23.5 | 3.7 | 1.1 | 2.7 | 30.5 | 13 |
| 110 | Acetone | 400:1 | 6.7 | 68.3 | 6.0 | 0.9 | 0.5 | 2.5 | 15.2 | a |
| 111 | Acetone | 500:1 | 10.3 | 68.7 | 6.1 | 0.0 | 0.0 | 1.9 | 13.0 | a |
| 112 | Acetone | 1600:1 | 16.4 | 32.9 | 22.3 | 2.4 | 1.3 | 1.1 | 23.6 | a |
| 113 | Acetone | 3600:1 | 17.5 | 45.0 | 18.4 | 1.5 | 2.8 | 2.1 | 12.7 | a |

Solvent + telogen = 25 ml, a ton was not determined

TABLE 6

Formulation same as in examples 1, with variable cocatalyst and Pd/P ratio

| Example | Cocatalyst | Pd/P | Proportion of telomer fraction/% | | | | | | | ton |
| | | | 1HT | 1TT | 1TH | 1HH | 3HT | 3TT | Other | |
|---|---|---|---|---|---|---|---|---|---|---|
| 114 | P(OCH2)3CCH2OH a | 1/1.2 | 29.3 | 61.1 | 5.8 | 0.7 | 1.9 | 0.4 | 0.9 | 313 |
| 115 | P(OCH2)3CCH2OH a | 1/2.1 | 35.6 | 53.6 | 5.9 | 0.8 | 2.7 | 1.1 | 0.4 | 518 |
| 116 | P(OCH2)3CCH2OH a | 1/4.7 | 24.3 | 26.7 | 12.8 | 21.2 | 0.0 | 0.0 | 15.1 | 5 |
| 117 | P(OCH2)3CCH2OH a | 1/6.7 | n.d. | n.d. | n.d. | n.d. | n.d. | n.d. | n.d. | <1 |
| 118 | P(OBu)3 | 1/1.9 | 37.1 | 37.1 | 15.4 | 1.7 | 2.8 | 1.0 | 1.2 | 277 |
| 119 | P(OBu)3 | 1/4.0 | 39.7 | 39.7 | 17.7 | 2.2 | 2.7 | 1.4 | 0.8 | 344 |
| 120 | P(OBu)3 | 1/5/7 | 28.6 | 28.6 | 18.4 | 3.2 | 1.6 | 1.6 | 25.9 | 6 | a t = 1 h

What is claimed is:

1. A process for preparing 6,10- and 6,9- dimethyl-5,10-undecadienyl-2-ones by telomerzing isoprene with alkyl acetoacetates in the presence of a catalyst system containing a transition metal compound catalyst and a phosphorus- or arsenic-containing compound cocatalyst, wherein the process is performed in the presence of a protic additive of the general formula $$R^1\text{—OH,}\tag{I}$$

or

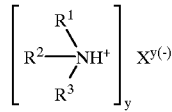 (II)

in which:
R$^1$, R$^2$, R$^3$ represent an alkyl group with 1 to 9 carbon atoms, branched or unbranched, a cycloalcyl group with 6 to 8 carbon atoms, an aryl group, or an arylalkyl group,
X$^{(-)}$ represents an inorganic or organic anion,
y is 1 or 2,
and the β-ketoester so obtained is saponified and decarboxylated in a manner known per se.

2. The process according to claim 1, wherein aliphatic carboxylic acids with 1 to 6 carbon atoms, arylsulfonic acids or alkysulfonic acids are used in addition to, or instead of, the protic additives of formulae (I) or (II).

3. The process according to claim 1, wherein at least two equivalents of isoprene are reacted with one equivalent of an alkyl acetoacetate of the general formula

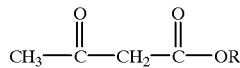 (III)

in which
R represents a C$_1$–C$_4$ alkyl group, branched or unbranched.

4. A process according to claim 1, wherein, the catalyst system consists of a transition metal compound from groups 9 and 10 of the Periodic System of Elements (ITUPAC 1985), and a cocatalyst consisting of a compound of the general formula

 (IV)

in which
R$^4$, R$^5$, R$^6$ are identical or different and represent an alkyl or alkoxy group with 1 to 8 carbon atoms, branched or unbranched, a cycloakyl group with 6 to 8 carbon atoms, an aryl group, optionally substituted, an arylalkyl group, or hydrogen;
A represents phosphorus or arsenic.

5. The process according to claim 4, wherein at least one of the substituents R$^4$, R$^5$, R$^6$ is itself substituted by one of the substituents selected from the group consisting of —OH, —NR$^1$H, —NR$^1$R$^2$H(+) and —COOH.

6. A process according to claim 1, wherein an acetate, carboxylate, carbonate, borate, citrate, bromide, chloride, iodide, hydroxide, nitrate, sulfate, arylsulfonate, acetylacetonate is used as a transition metal ligand in a transition metal compound.

7. The process according to claim 1, wherein the reaction is performed in the presence of a compound which acts as a reducing agent for the transition metal.

8. The process according to claim 7, wherein the reducing agent is selected from the group consisting of sodium borohydride, potassium borohydride, zinc powder or magnesium.

9. The process according to claim 4, wherein 1 to 10 equivalents of one or more compounds according to formula IV are used to one equivalent of said transition metal.

10. The process according to claim 7, wherein the amount of said transition metal used for the reaction is sufficient to provide up to 10$^{-4}$ to 1 g atom/l of elemental metal.

11. The process according to claim 1, wherein the reaction is performed at a temperature of from 0° C. to 130° C.

12. The process according to claim 1, wherein the process is performed in an organic solvent.

13. The process according to claim 12, wherein a compound of the formula (I), optionally mixed with non-protic solvents, is used as solvent.

14. The process according to claim 1, wherein the 6,10-dimethyl-5,10-undecadienyl-2-one and 6,9-dimethyl-5,10-undecadienyl-2-one are separated from the reaction mixture.

15. The process according to claim 4, wherein the aryl group is unsubstituted phenyl.

16. The process according to claim 4, wherein the aryl group is a phenyl substituted in the 2-position and/or 5-position with an alkyl group.

17. The process according to claim 6, wherein the transition metal compound contains palladium.

18. The process according to claim 1, wherein the reaction is performed at a temperature of from 60° C. to 100° C.

19. The process according to claim 1, further comprising saponifying and decarboxylating the β-ketoester.

20. A process for preparing 6,10- and 6,9-dimethyl-5,10-undecadienyl-2-ones by telomerizing isoprene with alkyl acetoacetates in the presence of a catalyst system containing a transition metal compound catalyst and a phosphorus- or an arsenic-containing compound cocatalyst, wherein the process is performed in the presence of an acid or a protic additive of the general formula:

 (I)

or

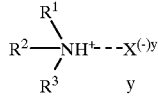 (II)

in which:

R$^1$, R$^2$, R$^3$ are selected from the group consisting of an alkyl group with 1 to 9 carbon atoms, branched or unbranched, a cycloalkyl group with 6 to 8 carbon atoms, an aryl group, a phenyl group, and an arylalkyl group, X$^{(-)}$ represents an inorganic or organic anion, y is 1 or 2 to form an enhanced yield of an 11-membered β-ketoester.

* * * * *